United States Patent [19]
Zilch et al.

[11] Patent Number: 5,512,564
[45] Date of Patent: Apr. 30, 1996

[54] TRICYCLIC THIAZOLE AND OXAZOLE DERIVATIVES AND PHARMACEUTICAL AGENTS CONTAINING THEM

[75] Inventors: Harald Zilch, Mannheim; Herbert Leinert, Heppenheim; Alfred Mertens, Schriesheim, all of Germany

[73] Assignee: Boehringer Mannheim GmbH, Mannheim, Germany

[21] Appl. No.: 193,056

[22] PCT Filed: Sep. 2, 1992

[86] PCT No.: PCT/EP92/02015

§ 371 Date: Mar. 4, 1994

§ 102(e) Date: Mar. 4, 1994

[87] PCT Pub. No.: WO93/05047

PCT Pub. Date: Mar. 18, 1993

[30] Foreign Application Priority Data

Sep. 7, 1991 [DE] Germany ............... 41 29 779.2

[51] Int. Cl.⁶ ................ C07D 498/14; A61K 31/425
[52] U.S. Cl. ............. 514/224.5; 514/248; 514/293; 514/250; 514/338; 514/366; 544/34; 544/234; 546/81; 546/271; 548/151
[58] Field of Search ............... 544/234, 34; 546/81, 546/271; 548/151; 514/224.5, 248, 293, 250, 338, 366

[56] References Cited

U.S. PATENT DOCUMENTS

| | | | |
|---|---|---|---|
| 2,860,985 | 11/1958 | Dann et al. | 540/611 |
| 3,334,113 | 8/1967 | Houlihan et al. | 548/302.4 |
| 3,646,022 | 1/1972 | Graf et al. | 544/48 |

OTHER PUBLICATIONS

Meyers, Tetrahedron Letters, vol. 30. No. 14, 1989, pp 1745–1748.
Bycroft et al, Tetrahedron Letters, vol. 24, No. 6, 1983, pp. 601–604.
Kurihara et al., Journal of Heterocyclic Chemistry, vol. 17, No. 5, Jul. 1980, pp. 945–951.
Hassan et al, Arch. Pharm. (Weinheim), vol. 324, No. 1, 1991, pp. 185–187.
Hassan et al, Chemical Abstracts, vol. 114, No. 21, Abstract No. 207,201j, p. 325, May 27, 1991.

*Primary Examiner*—C Warren Ivy
*Assistant Examiner*—Zinna N. Davis
*Attorney, Agent, or Firm*—Nikaido, Marmelstein, Murray & Oram

[57] ABSTRACT

The present invention concerns thiazolo-[2,3-a]pyrrole and oxazolo-[1,2-a]pyrrole derivatives of formula I

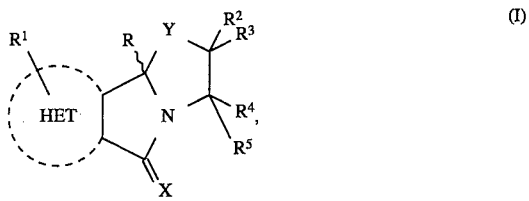

in which
HET represents a heterocyclic ring with 3–7 ring atoms which can be substituted by one, two or three residues $R^1$ which can be the same or different,
Y represents an oxygen or sulphur atom, or a SO or $SO_2$ group,
X can be an oxygen or sulphur atom,
R denotes an aliphatic residue with 1–9 C-atoms which can be substituted by phenyl or denotes a phenyl ring or a carbocyclic ring with 7–15 C atoms or a heterocyclic ring system each having 5 or 6 ring atoms,
in which the aforementioned phenyl rings, carbocyclic rings or heterocyclic ring system can be substituted once or several times, if desired, and R1–R5 denote hydrogen or an aliphatic residue, as well as their tautomers, enantiomers, diastereomers and physiologically tolerated salts.

19 Claims, No Drawings

TRICYCLIC THIAZOLE AND OXAZOLE DERIVATIVES AND PHARMACEUTICAL AGENTS CONTAINING THEM

This application is a 371 of PCT/EP92/0215 filed Sep. 2, 1992.

The present invention concerns tricyclic thiazole and oxazole derivatives, processes for their production and pharmaceutical agents which contain these compounds.

The invention concerns tricyclic thiazolo-[2,3-a]pyrrole and oxazolo-[1,2-a]pyrrole derivatives of formula I

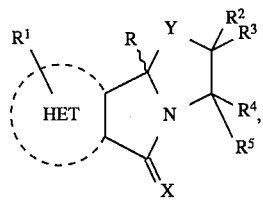

in which

HET represents an aromatic, partially hydrogenated or hydrogenated heterocyclic ring with 3–7 ring atoms of which up to four atoms can be heteroatoms in which the heteroatoms can be the same or different and denote oxygen, nitrogen or sulphur, and the heterocycles can, if desired, carry an oxygen atom on one or several nitrogen atoms and HET can be substituted by one, two or three residues $R^1$ which can be the same or different, Y represents an oxygen or sulphur atom, or a SO or $SO_2$ group, X can be an oxygen or sulphur atom, R denotes a straight-chained or branched, saturated or unsaturated aliphatic residue with 1–9 C atoms which can be substituted by phenyl or denotes a phenyl ring or a mono, bi or tricyclic carbocyclic ring with 7–15 C atoms or a heterocyclic mono, bi or tricyclic ring system each having five or six ring atoms and each ring system can contain 1–4 or 1–5 heteroatoms and the heteroatoms are nitrogen, sulphur or oxygen, in which the heteroatoms nitrogen and sulphur can, if desired, be substituted by oxygen atoms, and the aforementioned phenyl rings, the mono, bi or tricyclic carbocyclic rings or the heterocyclic mono, bi or tricyclic ring system is substituted, if desired, once or several times by $C_1$-$C_6$ alkyl, $C_1$-$C_6$ alkoxy, $C_1$-$C_6$ alkylmercapto, $C_1$-$C_6$-alkylsulfinyl, $C_1$-$C_6$ alkylsulfonyl, $C_2$-$C_6$ alkenyl, $C_2$-$C_6$ alkinyl, $C_2$-$C_6$ alkenyloxy, $C_2$-$C_6$-alkenylmercapto, $C_2$-$C_6$ alkinyloxy, $C_2$-$C_6$ alkinylmercapto, amino, $C_1$-$C_6$ alkylamino, di-$C_1$-$C_6$ alkylamino, $C_1$-$C_6$ alkylcarbonylamino, $C_1$-$C_6$ alkylaminocarbonyl, $C_1$-$C_6$ alkoxycarbonyl, hydroxy, benzyloxy, phenylmercapto, phenyloxy, nitro, cyano, halogen, trifluoromethyl, azido, formylamino, carboxy or phenyl, $R^1$ denotes a hydrogen atom, a straight-chained or branched, saturated or unsaturated aliphatic residue with 1–6 C atoms or $C_1$-$C_6$ alkoxy, $C_1$-$C_6$ alkylmercapto, $C_1$-$C_6$ alkylsulfinyl, $C_1$-$C_6$ alkylsulfonyl, amino, $C_1$-$C_6$ alkylamino, di-$C_1$-$C_6$ alkylamino, sulfonamido, $C_1$-$C_6$ alkoxycarbonyl, carboxy, halogen, hydroxy, nitro, cyano, azido, phenyl or benzyloxy, $R^2$ denotes hydrogen, $C_1$-$C_6$ alkyl, $C_1$-$C_6$ alkoxy, $C_1$-$C_6$ alkylmercapto, amino, $C_1$-$C_6$ alkylamino, di-$C_1$-$C_6$ alkylamino, halogen, cyano, hydroxy, carboxy, $C_1$-$C_6$ alkoxycarbonyl, aminocarbonyl or $C_1$-$C_6$ alkylaminocarbonyl, $R^3$, $R^4$, $R^5$ have the same meaning as $R^2$ and the residues $R^2$, $R^3$, $R^4$ and $R^5$ can independently of one another be the same or different, and $R^3$ with $R^4$ can, if desired, represent a double bond, as well as their tautomers, enantiomers, diastereomers and physiologically tolerated salts.

Thiazolo-[2,3-a]isoindoles are known as antiviral pharmaceutical agents from the earlier German Patent Application P 40 35 809.7.

The object of the present invention was to provide new tricyclic thiazolo-[2,3-a]pyrroles and oxazolo-[1,2-a] pyrroles with pharmacological properties. This object is achieved by the features characterized in the claims.

The compounds of the present invention have valuable pharmacological properties. In particular, they have an antiviral action and are suitable for the therapy and prophylaxis of infections that are caused by DNA viruses such as e.g. the herpes simplex virus, the cytomegaly virus, papilloma viruses, the varicella-zoster virus or Epstein-Barr virus or RNA viruses such as Toga viruses or in particular retroviruses such as the oncoviruses HTLV-I and II as well as the lentiviruses visna and human immunodeficiency virus HIV-1 and -2.

The compounds of formula I appear to be particularly suitable for the treatment of clinical manifestations of retroviral HIV infection in humans such as persistent generalized lymphadenopathy (PGL), the advanced stage of the AIDS related complex (ARC) and the complete clinical picture of AIDS.

The compounds according to the invention of the general formula I have a pronounced antiviral action and are especially suitable for the treatment of viral and retroviral infections. Viral infections of mammals, in particular of humans, are widespread. Despite intensive efforts, it has previously not been possible to provide chemotherapeutic agents which interfere causally or symptomatically with the course of the viral or retroviral disease with recognizable substantial success. Nowadays it is not possible to heal particular viral diseases such as for example the acquired immune deficiency syndrome (AIDS), the AIDS-related complex (ARC) and their precursor stages, herpes, cytomegaly virus (CMV), influenza and other viral infections or to favourably influence their symptoms by chemotherapy. At present 3'-azido-3'-deoxythymidine (AZT) known as Zidovudine or Retrovir® is for example almost all that is available for the treatment of AIDS. However, AZT is characterized by a very narrow therapeutic range and by very severe toxicities which occur even in the therapeutic range (Hirsch, M. S. (1988) J. Infec. Dis. 157, 427–431). The compounds of the general formula I do not have these disadvantages. They act antivirally without being cytotoxic in pharmacologically relevant doses.

It has now been possible to prove that compounds of the general formula I inhibit the multiplication of DNA and RNA viruses at the level of virus-specific DNA or RNA transcription. The substances are able to influence the multiplication of retroviruses by inhibiting the enzyme reverse transcriptase (cf. Proc. Natl. Acad. Sci. USA 83, 1911, 1986 or Nature 325, 773, 1987)

Since there is a very great need for chemotherapeutic agents which interfere as specifically as possible with diseases caused by retroviruses or with their symptoms without influencing the normal progress of natural body functions, the said compounds could be used advantageously, either prophylactically or therapeutically, in the treatment of diseases in which a retroviral infection is of pathophysiological, symptomatic or clinical relevance.

The resolution of the racemates into enantiomers can be carried out analytically, semipreparatively or preparatively by chromatography on suitable optically active phases using common eluting agents.

Optically active polyacrylamides or polymethacrylamides, partly also on silica gel (e.g. ChiraSpher® from Merck, Chiralpak® OT/OP from Baker), cellulose esters/carbamates (e.g. Chiracel® OB/OY from Baker/Daicel), phases based on cyclodextrin or crown ether (e.g. Crownpak® from Daicel) or microcrystalline cellulose triacetate (Merck) are for example suitable as optically active phases.

The anellated aromatic, partially hydrogenated or hydrogenated heterocyclic ring HET has 3–7 carbon atoms and 1–4 of these ring atoms can be replaced by the heteroatoms oxygen, sulphur and/or nitrogen. The following heterocycles are mentioned as examples: the aziridine, furan, tetrahydrofuran, thiophene, thiolan, sulfonal, pyrrole, pyrrolidine, oxazole, oxazoline, isoxazole, thiazole, thiazolidine, pyrazole, pyrazoline, imidazole, imidazoline, oxadiazole, furan, thiazole, pyridine, piperidine, morpholine, thiazine, pyridazine, pyrimidine, pyrazine, piperazine or azepine ring as well as their N-oxides.

In the case of partially hydrogenated rings, one or two double bonds of the aromatic system can be preferably hydrogenated so that the corresponding dihydro or tetrahydro derivatives result. HET can be preferably substituted by one or two residues $R^1$ which, independently of each other, can be the same or different.

An aliphatic residue in the definition of R and $R^1$ denotes a straight-chained or branched alkyl, alkenyl or alkinyl residue with 1–9, preferably 2–7 carbon atoms such as e.g. a propyl, isopropyl, butyl, isobutyl, pentyl, hexyl or heptyl residue. $C_2$-$C_7$ alkenyl and alkinyl residues come into consideration as unsaturated residues and preferably $C_2$-$C_5$ such as e.g. the allyl, dimethylallyl, butenyl, isobutenyl, pentenyl or propinyl residue.

An aliphatic residue which can be substituted by phenyl is in particular a phenyl-$C_1$-$C_6$-alkyl group such as e.g. the benzyl, phenethyl, phenylpropyl or phenylbutyl residue.

The phenyl rings mentioned in the definition of R can be substituted once, twice or three times. The substituents can independently of each other, be in the o, m or p position.

A carbocyclic ring with 7–15 C atoms can be mono, bi or tricyclic and have 5 or 6 C atoms in each case per ring. This ring can be saturated, unsaturated, partially saturated or aromatic. The following ring systems are mentioned as examples: the naphthyl, anthracenyl, phenanthrenyl, flourenyl, indenyl, acenaphthylenyl, norbornyl, adamantyl ring or a $C_3$-$C_7$ cycloalkyl or $C_5$-$C_8$ cycloalkenyl group. In addition the carbocyclic ring can be mono or disubstituted in which case the substituents can be preferably located independently of each other in the o or m position.

The heterocyclic mono, bi or tricyclic ring systems of the residue R contain 5 or 6 carbon atoms per ring in which 1–4 or 1–5 C atoms can be replaced by the heteroatoms oxygen, sulphur and/or nitrogen. The ring systems can be aromatic, partially or completely hydrogenated. The following ring systems are mentioned as examples: the pyridine, pyrimidine, pyridazine, pyrazine, triazine, pyrrole, pyrazole, imidazole, triazole, thiazole, oxazole, isoxazole, oxadiazole, furazan, furan, thiophene, indole, quinoline, isoquinoline, coumarone, thionaphthene, benzoxazole, benzthiazole, indazole, benzimidazole, benztriazole, chromene, phthalazine, quinazoline, quinoxaline, methylenedioxybenzol, carbazole, acridine, phenoxazine, phenothiazine, phenazine or the purine system as well as their N-oxides in which the saturated or aromatic carbocycles and heterocycles can be partially or completely hydrogenated. In addition the heterocyclic ring system can be mono or disubstituted in which case the substituents can be preferably independently of each other located in the o or m position.

R preferably denotes an unsubstituted phenyl or phenyl substituted once or twice by $C_1$-$C_3$ alkyl, $C_1$-$C_3$ alkoxy, $C_1$-$C_3$ alkylmercapto, $C_1$-$C_3$ alkylsulfinyl, $C_1$-$C_3$ alkylsulfonyl, $C_2$-$C_4$ alkenyl, $C_2$-$C_3$ alkinyl, $C_3$-$C_4$ alkenyloxy, $C_1$-$C_3$ alkylamino, $C_1$-$C_3$ dialkylamino, $C_1$-$C_3$ alkylcarbonylamino, $C_1$-$C_3$ alkylaminocarbonyl, $C_1$-$C_3$ alkoxycarbonyl, amino, hydroxy, nitro, azido, trifluoromethyl, cyano or halogen.

Carbocyclic rings are preferably biphenyl, naphthyl, anthracenyl, indenyl, fluorenyl, acenaphthylenyl, phenanthrenyl, norbornyl, adamantyl, $C_3$-$C_6$ cycloalkyl, $C_5$-$C_8$ cycloalkenyl in which the carbocyclic rings can be substituted once or twice by $C_1$-$C_3$ alkyl, $C_1$-$C_3$ alkoxy, $C_1$-$C_3$ alkylmercapto, $C_1$-$C_3$ alkylsulfinyl, $C_1$-$C_3$ alkylsulfonyl, $C_2$-$C_4$ alkenyl, $C_2$-$C_3$ alkinyl, $C_3$-$C_4$ alkenyloxy, $C_1$-$C_3$ alkylamino, $C_1$-$C_3$ dialkylamino, $C_1$-$C_3$ alkylcarbonylamino, $C_1$-$C_3$ alkylaminocarbonyl, $C_1$-$C_3$ alkoxycarbonyl, amino, hydroxy, nitro, azido, trifluoromethyl, cyano or halogen.

Heterocyclic ring systems of the residue R are preferably pyrrole, imidazole, furan, thiophene, pyridine, pyrimidine, thiazole, triazine, indole, quinoline, isoquinoline, coumarone, thionaphthene, benzimidazole, quinazoline, methylenedioxybenzol, ethylenedioxybenzol, carbazole, acridine and phenothiazine in which the heterocyclic rings can be substituted once or twice by $C_1$-$C_3$ alkyl, $C_1$-$C_3$ alkoxy, $C_1$-$C_3$ alkylmercapto, $C_1$-$C_3$ alkylsulfinyl, $C_1$-$C_3$ alkylsulfonyl, $C_2$-$C_4$ alkenyl, $C_2$-$C_3$ alkinyl, $C_3$-$C_4$ alkenyloxy, $C_1$-$C_3$ alkylamino, $C_1$-$C_3$ dialkylamino, $C_1$-$C_3$ alkylcarbonylamino $C_1$-$C_3$ alkylaminocarbonyl, $C_1$-$C_3$ alkoxycarbonyl, amino, hydroxy, nitro, azido, trifluoromethyl, cyano or halogen.

Hydrogen, $C_1$-$C_3$ alkyl, $C_2$-$C_4$ alkenyl, $C_2$-$C_4$ alkinyl, $C_1$-$C_3$ alkoxy, $C_1$-$C_3$ alkylmercapto, $C_1$-$C_3$ alkylamino, $C_1$-$C_3$ alkoxycarbonyl, amino, halogen, hydroxy, cyano and azido are preferred for the residue $R^1$.

Preferred substituents for $R^2$, $R^3$, $R^4$ and $R^5$ are hydrogen, $C_1$-$C_3$ alkyl, $C_1$-$C_3$ alkoxy, $C_1$-$C_3$ alkylmercapto, carboxy, $C_1$-$C_3$ alkoxycarbonyl, aminocarbonyl, $C_1$-$C_6$ alkylaminocarbonyl, halogen, cyano and hydroxy as well as a double bond in the ring formed jointly by $R^3$ and $R^4$.

X is preferably oxygen, Y preferably equals oxygen and sulphur. Halogen is generally understood as fluorine, chlorine, bromine and iodine, preferably fluorine, chlorine and bromine.

Preferred anellated heterocycles HET are aromatic, partially hydrogenated or hydrogenated rings containing nitrogen with 3–7 ring atoms, particularly preferably with 5 or 6 ring atoms.

Particularly preferred residues for R are $C_3$-$C_5$ alkyl, $C_2$-$C_5$ alkenyl, $C_2$-$C_4$ alkinyl, benzyl, phenethyl, phenyl, phenyl which is mono or disubstituted by $C_1$-$C_3$ alkyl, $C_1$-$C_3$ alkoxy, $C_1$-$C_3$ alkylmercapto, allyl, allyloxy, $C_1$-$C_3$ alkylamino, di-$C_1$-$C_3$ alkylamino, amino, hydroxy, azido, trifluoromethyl, cyano or halogen, and phenyl, naphthyl, anthracenyl, indenyl, acenaphthylenyl, phenanthrenyl, adamantyl, cyclohexyl, cylcohexenyl, furyl, thienyl, pyridyl, pyrimidinyl, thiazolyl, indolyl, quinolinyl, benzimidazolyl, methylenedioxyphenyl, carbazolyl and phenothiazinyl trisubstituted by methyl or halogen and derivatives of the aforementioned carbocyclic or heterocyclic rings which are mono or disubstituted by methyl or halogen.

Hydrogen, methyl, ethyl, isopropyl, allyl, methoxy, ethoxy, methylmercapto, ethylmercapto, methylamino, methoxycarbonyl, ethoxycarbonyl, amino, azido, cyano, hydroxy and halogen are particularly preferred for R1, chlorine and bromine being especially preferred for halogen.

Methyl, ethyl, isopropyl, methoxy, ethoxy, methylmercapto, ethylmercapto, methylamino, amino, chlorine, bromine and cyano are particularly preferred for $R^2$, $R^3$, $R^4$ and $R^5$.

A pyrrole, oxazole, isoxazole, thiazole, imidazole, pyridine, piperidine, pyridazine, pyrimidine and pyrazine ring is especially preferred for HET.

Compounds of formula I are especially preferred in which R, $R^1$, X and n have the meanings stated above and $R^2$, $R^3$, $R^4$ and $R^5$ are hydrogen, methyl, ethyl, chlorine, bromine, methoxy or ethoxy and $R^2$ to $R^5$ particularly preferably represent hydrogen or $R^2$ to $R^4$ are hydrogen and $R^5$ represents $C_1$-$C_4$ alkoxycarbonyl, aminocarbonyl or $C_1$-$C_3$ alkylaminocarbonyl.

Compounds of formula I are especially preferred in which $R^3$ and $R^4$ together represent a double bond, $R^2$ is a hydrogen atom and $R^5$ has the aforementioned meaning.

The pharmaceutical agents containing at least one compound of formula I for treating viral infections can be administered enterally or parenterally in a liquid or solid form. In this case the usual forms of administration come into consideration such as for example tablets, capsules, coated tablets, syrups, solutions or suspensions. Water is preferably used as an injection medium which contains the usual additives for injection solutions such as stabilizing agents, solubilizers and buffers. Such additives are for example tartrate and citrate buffer, ethanol, complexing agents such as ethylenediamine tetraacetic acid and their non-toxic salts, high molecular polymers such as liquid polyethylene oxide to regulate viscosity. Liquid vehicles for injection solutions must be sterile and are preferably dispensed into ampoules. Solid vehicles are for example starch, lactose, mannitol, methylcellulose, talcum, highly dispersed silicic acids, high molecular fatty acids such as stearic acid, gelatins, agar—agar, calcium phosphate, magnesium stearate, animal and vegetable fats, solid high molecular polymers such as polyethylene glycols etc. Suitable preparations for oral administration can, if desired, contain flavourings or sweeteners.

The dosage can depend on various factors such as type of application, species, age or individual state. The compounds according to the invention are usually administered in amounts of 0.1–100 mg, preferably 0.2–80 mg per day and per kg body weight. It is preferable to divide the daily dose into 2–5 applications, 1–2 tablets with a content of active substance of 0.5– 500 mg being administered in each application. The tablets can also be retarded and as a result the number of applications per day decreases to 1–3 per day. The content of active substance in the retarded tablets can be 2–1000 mg. The active substance can also be administered by continuous infusion in which case amounts of 5–1000 mg per day are usually adequate.

The compounds of the present invention and their pharmaceutical compositions can also be used in combination with other pharmaceutical agents for the treatment and prophylaxis of the aforementioned infections. Examples of these other pharmaceutical agents include agents that can be used for the treatment and prophylaxis of HIV infections or diseases which accompany this disease such as e.g. 3'-azido-3'-deoxythymidine; 2', 3'-dideoxynucleosides such as e.g. 2', 3'-dideoxycytidine, 2', 3'-dideoxyadenosine or 2', 3'-dideoxyinosine; acyclic nucleosides (e.g. Acyclovir); interferones such as e.g. A interferone; inhibitors of renal excretion such as e.g. probenicid; nucleoside transport inhibitors such as e.g. dipyridamol; immunomodulators such as e.g. interleukin II or stimulating factors such as e.g. granulocyte macrophage colony factor. The compounds of the present invention and the other pharmaceutical agents can either be administered individually, simultaneously and if desired in a single or two separate formulations or at different times so that a synergistic effect is achieved.

The compounds according to the invention of the general formula I are produced according to processes known from the literature by reacting heterocyclic ketocarboxylic acids of the general formula II

in which R and $R^1$ have the meanings stated above and A is —COOH, with substituted or unsubstituted cysteamine or ethanolamine of the general formula III

in which Y is oxygen or sulphur and $R^2$, $R^3$, $R^4$ and $R^5$ have the meanings stated above, in a suitable inert solvent at room temperature to reflux temperature possibly in the presence of catalytic amounts of acid e.g. p-toluenesulfonic acid and if desired, compounds of formula I are subsequently converted into other compounds of formula I and subsequently purified by chromatography or recrystallization. Racemates can be resolved into the antipodes by chromatography on suitable optically active phases e.g. cellulose triacetate.

The subsequent conversions of compounds of formula I into other compounds of formula I relates for example to the production of tricyclic thiazolo-[2,3-a]pyrrole derivatives in which X=S. Compounds in which X=S are produced by reacting compounds of formula I, in which X denotes an oxygen atom, with compounds that transfer sulphur groups such as e.g. Lawesson's reagent.

Some of the ketocarboxylic acid derivatives of the general formula II are known from the literature and are produced for example by Friedel-Crafts acylation of substituted or unsubstituted anhydrides of heterocyclcic dicarboxylic acids of formula IV

in which $R^1$ and HET have the meanings stated above, with arenes which are substituted if desired, in the presence of a Lewis acid (e.g. aluminium chloride) or by reacting Grignard reagents of the general formula V

or lithium-organic compounds of the general formula VI

in which R has the meaning stated above with the exception of hydrogen, with appropriate anhydrides which are substituted if desired, in suitable inert solvents at low temperatures.

The compounds of formula III are known in the literature or can be produced in an analogous manner to the known processes. Some derivatives are also commercially available.

The processes for the production of the compounds according to the invention of the general formula I are carried out analogously to processes described in the following applications or literature references: U.S. Pat. No. 3,334,113, CH-469,733, Belgian Patent Application 659,528 and U.S. Pat. No. 3,646,022, U.S. Pat. No. 2,860,985, Belgian Patent Application 564,592, J. Org. Chem. 30, 1506 (1965) as well as J. Org. Chem. 34, 165 (1969).

Apart from the compounds mentioned in the examples and those which result by combining all meanings for the substituents mentioned in the claims, the following compounds of formula I come into consideration within the meaning of the invention which may be present as racemic mixtures or in an optically active form or as pure R and S enantiomers:

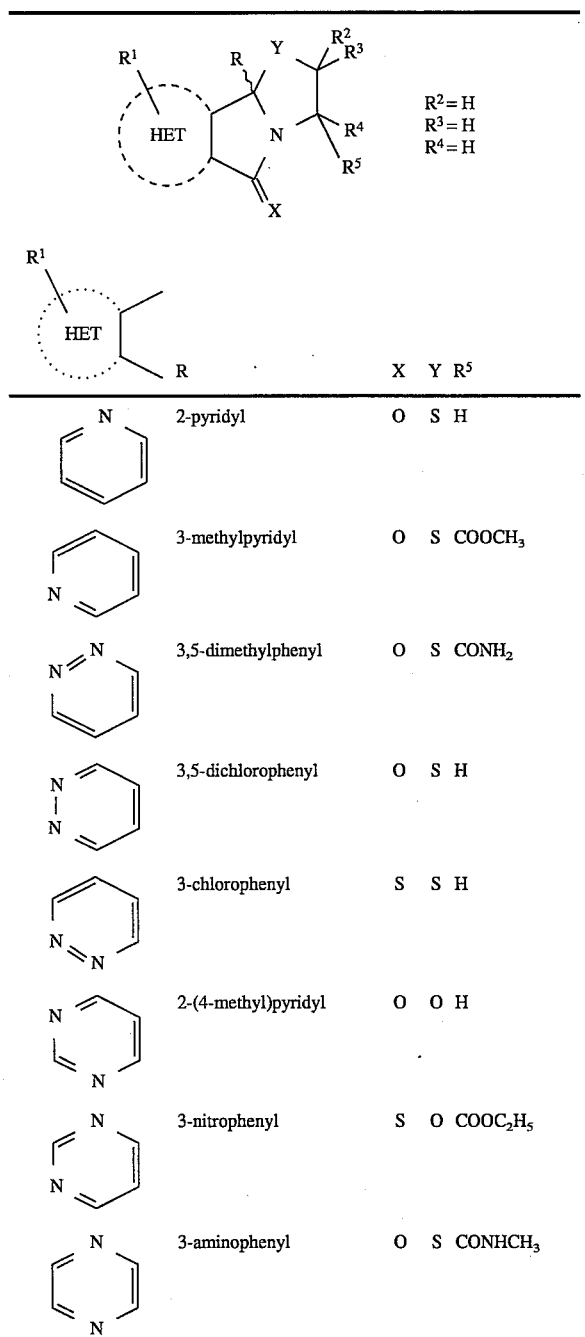

| HET | R | X | Y | $R^5$ |
|---|---|---|---|---|
| N (2-pyridyl ring) | 2-pyridyl | O | S | H |
| 3-pyridyl ring | 3-methylpyridyl | O | S | $COOCH_3$ |
| pyridazinyl | 3,5-dimethylphenyl | O | S | $CONH_2$ |
| pyrazolyl | 3,5-dichlorophenyl | O | S | H |
| pyridazinyl | 3-chlorophenyl | S | S | H |
| pyrazinyl | 2-(4-methyl)pyridyl | O | O | H |
| pyrazinyl | 3-nitrophenyl | S | O | $COOC_2H_5$ |
| pyrazinyl | 3-aminophenyl | O | S | $CONHCH_3$ |
| furanyl | 3-methoxyphenyl | O | S | $COOC_3H_7$ |
| furanyl | phenyl | O | S | $COOCH_3$ |
| pyrrolyl (HN) | 2-(4,6-dimethyl)pyridyl | O | S | $COOCH_3$ |
| pyrrolyl (HN) | 2-(6-methyl)pyridyl | O | S | H |
| pyrrolyl (NH) | 2-(6-chloro)pyridyl | O | S | $COOC_4H_9$ |
| oxazolyl | 2-(4-chloro)pyridyl | S | S | $CONH_2$ |
| thiazolyl | 1-naphthyl | O | S | H |
| oxazolyl | 9-anthracenyl | O | S | $CONHC_2H_5$ |
| thiazolyl | 4-indanyl | O | S | H |
| oxazolyl | 2-(4-methyl)pyridyl | O | O | H |
| oxazolyl | 3-methylphenyl | O | S | H |
| thiazolyl | 2-chlorophenyl | O | S | H |
| pyrazolyl (HN-N) | 2-pyridyl | S | S | $CONH_2$ |

-continued

| | R | X | Y | R⁵ |
|---|---|---|---|---|
| pyrrole-NH (N-NH) | 2-(6-methyl)pyridyl | S | O | COOC₂H₅ |
| pyrrole-NH (N-NH) | 2-pyridyl | O | S | CONHCH₃ |
| thiomorpholine-NH (S...NH) | 2-(4-methyl)pyridyl | O | S | H |
| thiomorpholine-NH (NH...S) | 2-pyridyl | S | S | H |
| aziridine (HN△) | 3-methylphenyl | O | S | H |

EXAMPLE 1

3a-Phenyl-2,3a-Dihydro-1H-3-Thia-7,8a-Diaza-Cyclopenta[a]Inden-8-One a) 3-benzoylpyridine-2-carboxylic acid 10 g (67 mmol) quinolinic acid anhydride was suspended in 50 ml benzene and 17.9 g (134 mmol) AlCl₃ was added in portions while cooling on ice. After completion of the addition, it was stirred for a further 3 hours at room temperature, carefully admixed with ice and aspirated from the precipitate which was present. The crude product was purified by column chromatography on silica gel 60 using ethyl acetate/dichloromethane 1/1 as the eluent.

Yield 3.5 g (23% of theoretical yield)

b)

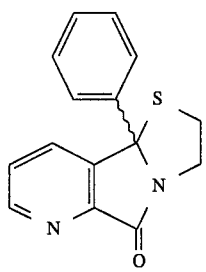

1.2 g (5 mmol) 3-benzoylpyridine-2-carboxylic acid in 50 ml toluene was admixed with 0.81 g (10 mmol) cysteamine and a catalytic amount of p-toluenesulfonic acid and heated under reflux for 16 hours. After cooling the solvent was removed in a vacuum and the residue was purified by column chromatography on silica gel 60 using acetic acid/isohexane 2/1. The desired fractions were concentrated by evaporation and the residue was recrystallized from ethanol. Yield 1.0 g (71% of theoretical yield), melting point 178°–179° C.

EXAMPLE 2

3a-Phenyl-2,3a-Dihydro-1H-3-Thia-4,8a-Diaza-Cyclopenta[a]Inden-8-One a) 2-benzoylpyridine-3-carboxylic acid 4.2 g quinolinic acid β methyl ester chloride was suspended in 40 ml benzene, 8.4 g AlCl₃ was added in portions at 80° C. and it was stirred at 80° C. for 4 hours. Then the solvent was removed in a vacuum, the residue was extracted with hot water and the insoluble residue was purified by column chromatography on silica gel 60 with acetic acid/10% methanol. Yield 1.42 g (30% of theoretical yield).

b)

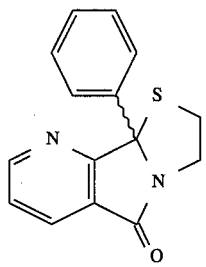

1.3 g 2-benzoylpyridine-3-carboxylic acid was reacted analogously to example 1 with 0.85 g cysteamine. Yield 0.4 g (26% of theoretical yield), melting point 172°–176° C. [cf. "Monatshefte d. Chem." 31, 295 (1910)].

EXAMPLE 3

3a-m-Tolyl-2,3a-Dihydro-1H-3-Thia-4,7,8a-Triaza-Cyclopenta[a]Inden-8-One a) 3-(m-methylbenzoyl)-pyrazine-2-carboxylic acid The Grignard reagent from 8.5 g (50 mmol) 3-bromotoluene and 1.2 g magnesium in 50 ml ether was added dropwise at 0°–10° C. to a solution of 7.5 g (50 mmol) pyrazine-2,3-dicarboxylic acid anhydride in 100 ml THF and after completed addition, the solution that formed was stirred for 4 hours at room temperature. 500 ml cold, saturated NH₄Cl solution was then added, it was extracted with ethyl acetate and the organic phase was dried, concentrated by evaporation and purified as in example 1a and 2a. Yield 4 g (32% of theoretical yield).

b)

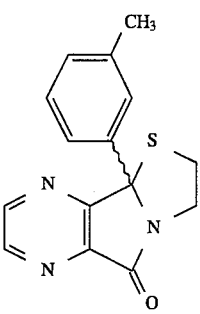

1.5 g 3-(m-methylbenzoyl)-pyrazine-2-carboxylic acid was reacted analogously to example 1 with 1.15 g cysteamine. Yield 300 mg (17% of theoretical yield), melting point 175° C.

EXAMPLE 4

3a-Phenyl-2,3a-Dihydro-1H-3-Thia-4,7,8a-Triaza-Cyclopenta[ a]Inden-8-One a) 3-benzyolpyrazine-3-carboxylic acid was produced analogously to example 3a by use of phenylmagnesium bromide in a yield of 56%.

b)

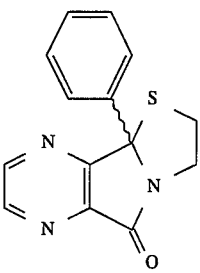

1.15 g 3-benzoylpyrazine-2-carboxylic acid was reacted analogously to example 1 with 1.1 g cysteamine in xylol. Yield 280 mg (20% of theoretical yield), melting point 213°–216° C.

EXAMPLE 5

3a-(3,5-Dimethyl-Phenyl)-2,3a-Dihydro-1H-3-Thia-4,7, 8a-Triaza-Cyclopenta[ a]Inden-8-One a) 3- (3,5-dimethylbenzyol)-pyrazine-2-carboxylic acid was produced analogously to example 3a by use of 3,5-dimethylphenylmagnesium bromide in a yield of 32%.

b)

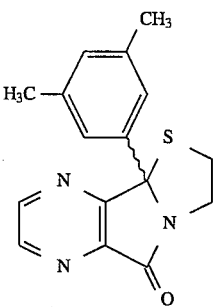

2.6 g 3-(3,5-dimethylbenzoyl)-pyrazine-2-carboxylic acid was reacted analogously to example 1 with 2 g cysteamine in xylol. Yield 805 mg (23% of theoretical yield), melting point 162°–165° C.

EXAMPLE 6

3a-Phenyl-2,3a-Dihydro-1H-3-Thia-6,8a-Diaza-Cyclopenta[ a]Inden-8-One a) 4-benzoylpyridine-3-carboxylic acid was prepared analogously to example 1a from 3,4-pyridine-dicarboxylic acid anhydride and separated from the 3-benzoylpyridine-4-carboxylic acid by fractional crystallization from ethanol. Yield 34 and 27% respectively of the theoretical yield.

b)

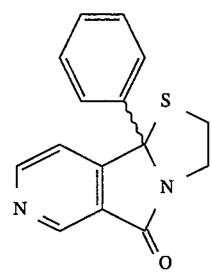

1 g 4-benzoylpyridine-3-carboxylic acid was reacted analogously to example 1 with 680 mg cysteamine. Yield 440 mg (37% of theoretical yield), melting point 120°–121° C.

EXAMPLE 7

3a-Phenyl-2,3a-Dihydro-1H-3-Thia-5,8a-Diaza-Cyclopenta[ a]Inden-8-One

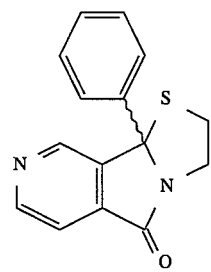

1.6 g of the 3-benzoylpyridine-4-carboxylic acid isolated in example 6a as a by-product was reacted with 1.08 g cysteamine analogously to example 1. Yield 1.24 g (66% of theoretical yield), melting point 228°–229° C.

EXAMPLE 8

3a-(4-Methyl-Pyridin-2-Yl)-2,3a-Dihydro-1H-3-Thia-4, 8a-Diaza-Cyclopenta[ a]Inden-8-One a)

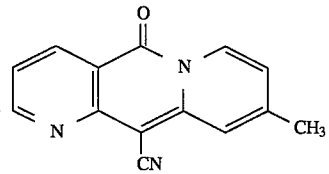

A solution of 9.7 g (73 mmol) 2-cyanomethyl-4-picoline in 25 ml ether was added dropwise within 15 minutes to a suspension of 3.8 g (0.146 mol) NaH in 75 ml absolute ether and heated for 1 hour under reflux. Then 13.5 g (73 mmol)

2-chloronicotinic acid methyl ester in 25 ml ether was added and it was heated for a further 3 hours under reflux. After cooling, the crystals which formed were aspirated and used in the next reaction without further purification.

b)

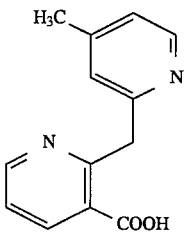

The crude product of the last reaction in 150 ml 6N HCl was stirred for 3 days in an autoclave at 130° C., the crystals were aspirated and it was recrystallized from ethanol. Yield 5.2 g (31% relative to 2-cyanomethyl-4-picoline), melting point 277°–279° C.

c)

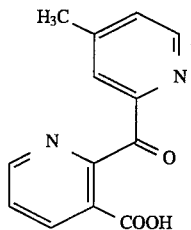

1.6 g (7 mmol) 2-(4-picolin-2-ylmethyl)nicotinic acid was dissolved with 1.6 g KMnO₄ in 32 ml water and heated for 3 hours to 95° C. Then the manganese dioxide was separated, the filtrate was concentrated by evaporation and the residue was purified by column chromatography on silica gel 60 using CH₂Cl₂/EtOH 8/2 as the eluent. Yield 1.6 g (65% of theoretical yield), melting point 210°–212° C.

d)

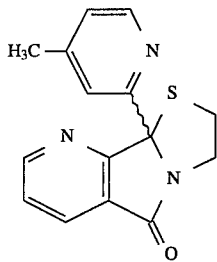

0.7 g (3.1 mmol) 2-(4-picolin-2-ylcarbonyl)-nicotinic acid was reacted with 0.5 g cysteamine analogously to example 1. Yield 0.3 g (34% of theoretical yield), melting point 129°–130° C.

EXAMPLE 9

3a-Pyridin-2-Yl-2,3a-Dihydro-1H-3-Thia-4,8a-Diaza-Cyclopenta[a]Inden-8-One a) 2-(2-pyridylcarbonyl)-nicotinic acid was produced analogously to example 8 starting with 2-cyanomethyl-pyridine.

b)

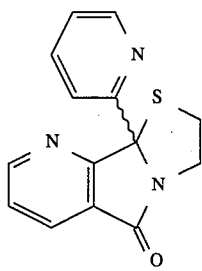

1.4 g 2-(2-pyridylcarbonyl)-nicotinic acid was reacted with 1 g cysteamine analogously to example 1. Yield 670 mg (41% of theoretical yield), melting point 149°–150° C.

EXAMPLE 10

3a-(6-Methyl-Pyridin-2-Yl)-2,3a-Dihydro-1H-3-Thia-4,8a-Diaza-Cyclopenta[a]Inden-8-One a) 2-(2-picolin-6-ylcarbonyl)-nicotinic acid was produced analogously to example 8 starting with 6-cyanomethyl-2-picoline.

b)

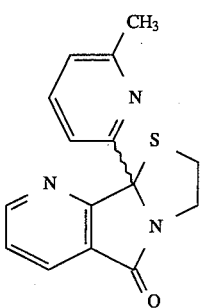

1 g 2-(2-picolin-6-ylcarbonyl)-nicotinic acid was reacted with 0.8 g cysteamine analogously to example 1. Yield 655 mg (56% of theoretical yield), melting point 134°–135° C.

EXAMPLE 11

3a-(4,6-Dimethyl-Pyridin-2-Yl)2,3a-Dihydro-1H-3-Thia-4,8a-Diaza-Cyclopenta[a]Inden-8-One a) 2-(2,4-lutidin-6-ylcarbonyl)-nicotinic acid was produced analogously to example 8 starting with 6-cyanomethyl- 2,4-lutidine.

b)

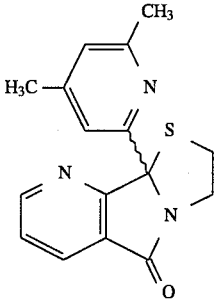

870 mg 2-(2,4-lutidin-6-ylcarbonyl)-nicotinic acid was reacted with 530 mg cysteamine analogously to example 1. Yield 414 mg (41% of theoretical yield), oil.

EXAMPLE 12

3a-(6-Methyl-Pyridin-2-Yl)-2,3a-Dihydro-1H-3-Oxa-4,8a-Diaza-Cyclopenta[a]Inden-8-One

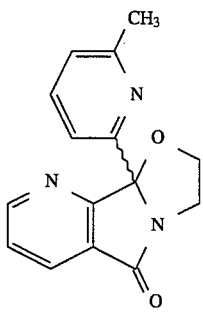

1.21 g 2-(2-picolin-6-ylcarbonyl)-nicotinic acid was reacted with 610 mg ethanolamine analogously to example 1. Yield 735 mg (55% of theoretical yield), melting point 234°–236° C.

EXAMPLE 13

3a-m-Tolyl-2,3a-Dihydro-1H-3-Thia-4,8a-Diaza-Cyclopenta[a]Inden-8-One a)

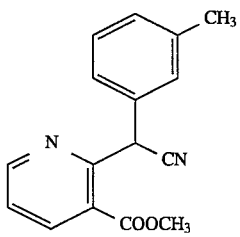

19.6 g (0.15 mol) m-methylbenzylcyanide in 25 ml ether was added dropwise within 15 minutes at room temperature to a suspension of 7.92 g (0.33 mol) NaH in 120 ml ether and heated for 1 hour under reflux. Then 25.7 g 2-chloronicotinic acid methyl ester in 25 ml ether was added dropwise at room temperature and heated for a further 2 hours under reflux. After cooling, the precipitate which formed was aspirated, washed with water and recrystallized from isopropanol, yield 31.2 g (78% of theoretical yield), melting point 108°–110° C.

b)

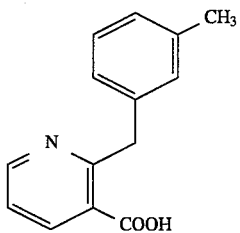

The hydrolysis of the nitrile of the last reaction was carried out analogously to example 8b. Yield 43% melting point 73°–77° C.

c)

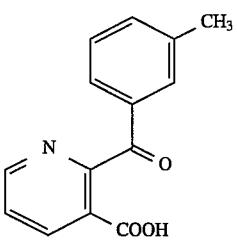

The oxidation of the 2-benzylnicotinic acid of the last reaction was carried out analogously to example 8c. Yield 51%, melting point 164°–166° C.

d)

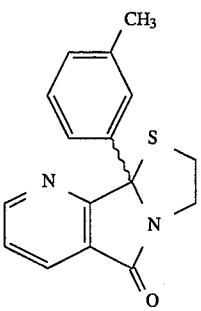

960 mg 2-(m-methylbenzoyl)-nicotinic acid was reacted with 620 mg cysteamine analogously to example 1. Yield 438 mg (39% of theoretical yield), melting point 119°–121° C.

EXAMPLE 14

1-Hydroxymethyl-3a-m-Tolyl-2,3a-Dihydro-1H-3-Thia-4,8a-Diaza-Cyclopenta[a]Inden-8-One

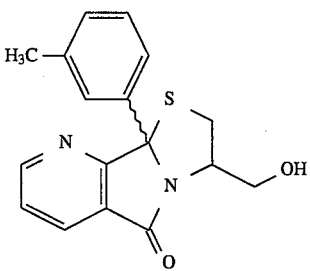

12 g (0.05 mol) 2-(methylbenzoyl)nicotinic acid (cf. example 13) was heated for 4 hours under reflux in the presence of 10.7 g (0.1 mol) cysteinol [cf. Helv. Chim. Acta Vol. XLIV, Fasciculus III, 706 (1961), No. 82; the crude product was used in the reaction] and 1.2 g p-toluenesulfonic acid in 250 ml toluene. After cooling, the toluene phase was extracted by shaking several times with saturated NaHCO₃ solution, washed with water, dried over Na₂SO₄ and concentrated by evaporation. The residue was purified by column chromatography on silica gel 60 using toluene/acetone 5/2 as the eluent. Yield 4.2 g (27% of theoretical yield).

EXAMPLE 15

1-Methyl-3a-m-Tolyl-3aH-3-Thia-4,8a-Diaza-Cyclopenta[a]Inden-8-One

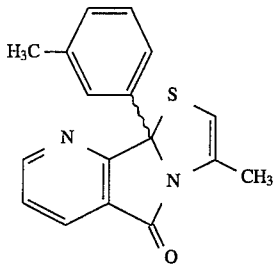

1.6 g (5.2 mmol) of the hydroxymethyl compound of example 14 in 30 ml absolute pyridine was slowly admixed with 2 g (10.3 mmol) p-toluenesulfonyl chloride and stirred under nitrogen for 24 hours at room temperature. The solvent was then removed, the residue was taken up in ethyl acetate and extracted twice by shaking with 2N HCl and saturated $NaHCO_3$ solution each time. The organic phase was dried, concentrated by evaporation and the residue was recrystallized from isopropanol.

Afterwards the tosylate was dissolved in 70 ml methanol, admixed with 0.3 ml 10N NaOH and 0.21 g imidazole and heated in an autoclave for 12 hours at 150° C. After cooling, the solvent was removed in a rotary evaporator and the residue was purified by column chromatography on a Chromatotron using toluene/methanol 5/1 as the eluent. Yield 350 mg (23% of theoretical yield).

EXAMPLE 16

Inhibition of Reverse Transcriptase

The screening test system comprises the purified RT from HIV-1 which was expressed by genetic engineering methods in *E. coli* as well as the components of the initiation complex and site complementary 18mer oligonucleotide as the primer. The [$^3$H]-thymidine-5'-triphosphate incorporation was measured by counting in a β counter. The $IC_{50}$ value is given in the following table for the investigated compounds. This value corresponds to that concentration of the test substance which causes a 50% inhibition of the RT activity.

Results

| Substance [example] | Inhibition of the HIV-RT $IC_{50}$ [M] |
|---|---|
| 2 | $3.3 \times 10^{-6}$ |
| 5 | $4.0 \times 10^{-5}$ |
| 7 | $1.7 \times 10^{-5}$ |
| 8 | $4.6 \times 10^{-6}$ |
| 9 | $2.3 \times 10^{-5}$ |
| 10 | $6.6 \times 10^{-6}$ |
| 11 | $3.9 \times 10^{-6}$ |
| 13 | $4.0 \times 10^{-6}$ |

We claim:
1. Pyrrole compounds of the formula

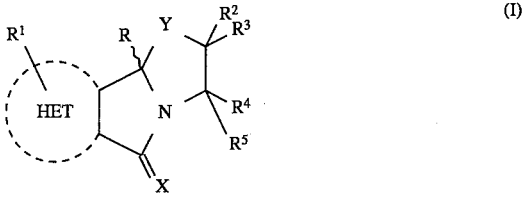

wherein

HET is a heterocyclic ring which is a member selected from the group consisting of aziridine, furan, tetrahydrofuran, thiophene, thiolan, sulfonal, pyrrole, pyrrolidine, oxazole, oxazoline, isoxazole, thiazole, thiozolidine, pyrazole, pyrazoline, imidazole, imidazoline, oxadiazole, furan, thiazole, pyridine, piperidine, morpholine, thiazine, pyridazine, pyrimidine, pyrazine, piperazine and azepine, and N-oxide, dihydro and tetrahydro hydrogenated rings of said member, wherein said member are substituted by at least one $R^1$ moiety;

$R^1$ is hydrogen, $C_1$-$C_6$ alkyl, $C_2$-$C_7$ alkenyl, $C_2$-$C_7$ alkinyl, $C_1$-$C_6$ alkoxy, $C_1$-$C_6$ alkylmercapto, $C_1$-$C_6$ alkylsulfinyl, $C_1$-$C_6$ alkylsulfonyl, amino, $C_1$-$C_6$ alkylamino di-$C_1$-$C_6$ alkylamino, sulfomamido, $C_1$-$C_6$ alkoxycarbonyl, carboxy, halogen, hydroxy, nitro, cyano, azido, phenyl or benzyloxy;

Y is oxygen, sulphur, SO or $SO_2$;

X is an oxygen or sulphur atom;

R is (a) $C_1$-$C_9$ alkyl, $C_2$-$C_7$ alkenyl or $C_2$-$C_7$ alkinyl, wherein said alkyl, alkenyl and alkinyl radicals, which can be straight-chained or branched, are unsubstituted or substituted by phenyl, b) phenyl or a mono, bi or tricyclic carbocyclic ring containing 7–15 ring carbon atoms, or c) a heterocyclic ring selected from the group consisting of the pyridine, pyrimidine, pyridazine, pyrazine, triazine, pyrrole, pyrazole, imidazole, triazole, thiazole, oxazole, isoxazole, oxadiazole, furazan, furan, thiophene, indole, quinoline, isoquinoline, coumarone, thionaphthene, benzoxazole, benzthiazole, indazole, benzimidazole, benztriazole, chromene, phthalazine, quinazoline, quinoxaline, methylenedioxybenzol, carbazole, acridine, phenoxazine, phenothiazine, phenazine and purine, and N-oxide, partially hydrogenated and completely hydrogenated Ring systems thereof, wherein the carbocyclic rings and the heterocyclic rings are unsubstituted or substituted by at least one substituent selected from the group consisting of $C_1$-$C_6$ alkyl, $C_1$-$C_6$ alkoxy, $C_1$-$C_6$ alkylmercapto, $C_1$-$C_6$ alkylsulfinyl, $C_1$-$C_6$ alkylsulfonyl, $C_2$-$C_7$ alkenyl, $C_2$-$C_7$ alkinyl, $C_2$-$C_7$ alkenyloxy, $C_2$-$C_7$ alkenylmercapto, $C_2$-$C_7$ alkinyloxy, $C_2$-$C_7$ alkinylmercapto, amino, $C_1$-$C_6$ alkylamino, di-$C_1$-$C_6$ alkylamino, $C_1$-$C_6$, alkyl-carbonylamino, $C_1$-$C_6$ alkylaminocarbonyl, $C_1$-$C_6$ alkoxycarbonyl, hydroxy, benzyloxy, phenylmercapto, phenyloxy, nitro, cyano, halogen, trifluoromethyl, azido, formylamino, carboxy and phenyl, $R^2$ is hydrogen, $C_1$-$C_6$ alkyl, $C_1$-$C_6$ alkoxy, $C_1$-$C_6$ alkylmercapto, amino, $C_1$-$C_6$ alkylamino, di-$C_1$-$C_6$ alkylamino, halogen, cyano, hydroxy, carboxy, $C_1$-$C_6$ alkoxycarbonyl, aminocarbonyl or $C_1$-$C_6$ alkylaminocarbonyl, $R^3$, $R^4$ and $R^5$, which are the same or different, have the same meanings as $R^2$, or $R^3$ and $R^4$ together represent a double bond;

or tautomers, enantiomers, diastereomers or a physiologically acceptable salt thereof.

2. Pyrrole compounds of claim 1, wherein HET is an aromatic 5- or 6- membered ring containing 1 or 2 nitrogen atoms.

3. Pyrrole compounds of claim 1, wherein HET is a 5- or 6-membered ring containing an oxygen atom or an oxygen atom and a nitrogen atom.

4. Pyrrole compounds of claim 1, wherein HET is a 5- or 6-membered ring containing a sulphur atom and a nitrogen atom.

5. Pyrrole compounds of claim 1, wherein $R^1$ is hydrogen, $C_1$-$C_7$ alkyl, $C_2$-$C_7$ alkenyl, $C_2$-$C_7$ alkinyl, $C_1$-$C_7$ alkoxy, $C_1$-$C_7$ alkylmercapto, $C_1$-$C_7$ alkylamino, $C_1$-$C_7$ alkoxycarbonyl, amino, halogen, hydroxy, cyano or azido.

6. Pyrrole compounds of claim 1, wherein R is a carbocyclic ring.

7. Pyrrole compounds of claim 1, wherein R is a heterocyclic ring.

8. Pyrrole compounds of claim 1, wherein R is a mono- or disubstituted or unsubstituted phenyl group.

9. Pyrrole compounds of claim 1, wherein R is a carbocyclic or heterocyclic ring, which ring is substituted by $C_1$-$C_7$ alkyl, $C_2$-$C_7$ alkenyl or $C_2$-$C_7$ alkinyl.

10. Pyrrole compounds of claim 1, wherein $R^2$, $R^3$, $R^4$ and $R^5$ are independently hydrogen or $C_1$-$C_6$ alkyl.

11. Pyrrole compounds of claim 1, wherein at least one of $R^2$, $R^3$ $R^4$ and $R^5$ is $C_1$-$C_6$ alkoxy, $C_1$-$C_6$ alkylmercapto, carboxy, $C_1$-$C_6$ alkoxycarbonyl, aminocarbonyl, $C_1$-$C_6$ alkylaminocarbonyl, halogen cyano or hydroxy.

12. Pyrrole compounds of claim 1, wherein the compound is 3a-phenyl-2,3a-dihydro-1H-3-thia-4,8a-diaza-cyclopenta[a]inden-8-one 3a-(4,6-dimethyl-pyridin-2-yl)-2,3a-dihydro- 1H-3-thia-4,8a-diaza-cyclopenta[a]inden-8-one or 3a-m-tolyl-2,3a-dihydro-1H-3-thia-4,8a-diaza-cyclopenta[a]inden-8-one 13. Pyrrole compounds of claim 1, wherein $R^1$ is hydrogen, $C_1$-$C_3$ alkyl, $C_2$-$C_4$ alkenyl, $C_2$-$C_4$ alkinyl, $C_1$-$C_3$ alkoxy, $C_1$-$C_3$ alkylmercapto, $C_1$-$C_3$ alkylamino, $C_1$-$C_3$ alkoxycarbonyl, amino, halogen, hydroxy, cyano or azido.

14. Pyrrole compounds of claim 1, wherein $R^2$, $R^3$, $R^4$ and $R^5$ are independently hydrogen, $C_1$-$C_3$ alkyl, $C_1$-$C_3$ alkoxy, $C_1$-$C_3$ alkylmercapto, carboxy, $C_1$-$C_3$ alkoxycarbonyl, aminocarbonyl, $C_1$-$C_6$ alkylaminocarbonyl, halogen, cyano or hydroxy, or $R^3$ and $R^4$ together form a double bond.

15. Pyrrole compounds of claim 1, wherein X is oxygen and Y is oxygen or sulphur.

16. Pyrrole compounds of claim 1, wherein R is $C_3$-$C_5$ alkyl, $C_2$-$C_7$ alkenyl, $C_2$-$C_4$ alkinyl, benzyl, phenethyl, phenyl, phenyl which is mono or disubstituted by $C_1$-$C_3$ alkyl, $C_1$-$C_3$ alkoxy, $C_1$-$C_3$ alkylmercapto, allyl, allyloxy, $C_1$-$C_3$ alkylamino, di-$C_1$-$C_3$ alkylamino, amino, hydroxy, azido, trifluoromethyl, cyano or halogen, phenyl, naphthyl, anthracenyl, indenyl, acenaphthylenyl, phenanthrenyl, adamantyl, cyclohexyl, cylcohexenyl, furyl, thienyl, pyridyl, pyrimidinyl, thiazolyl, indolyl, quinolinyl, benzimidazolyl, methylenedioxyphenyl, carbazolyl or phenothiazinyl trisubstituted by methyl or halogen, or benzyl, phenethyl, phenyl, naphthyl, anthracenyl, indenyl, acenaphthylenyl, phenanthrenyl, adamantyl, cyclohexyl, cyclhexenyl, furyl, thienyl, pyridyl, pyrimidinyl, thiazolyl, indolyl, quinolinyl, benzimidazolyl, methylenedioxyphenyl, carbazolyl, or phenothiazinyl which are mono or disubstituted by methyl or halogen.

17. Pyrrole compounds of claim 1, wherein $R^1$ is hydrogen, methyl, ethyl, isopropyl, allyl, methoxy, ethoxy, methylmercapto, ethylmercapto, methylamino, methoxycarbonyl, ethoxycarbonyl, amino, azido, cyano, hydroxy or halogen.

18. Pyrrole compounds of claim 1, wherein HET is pyrrole, oxazole, isoxazole, thiazole, imidazole, pyridine, piperidine, pyridazine, pyrimidine or pyrazine.

19. Pharmaceutical composition suitable for the treatment of viral diseases comprising a pyrrole compounds of claim 1 and a pharmaceutically acceptable carrier therefor.

\* \* \* \* \*